United States Patent
Estevez-Labori (10) Patent No.: US 7,613,583 B2
(45) Date of Patent: Nov. 3, 2009

(54) METHOD AND SYSTEM FOR PARTICLE DATA PROCESSING

(75) Inventor: Francisco Estevez-Labori, Miami Beach, FL (US)

(73) Assignee: Beckman Coulter, Inc., Fullerton, CA (US)

( * ) Notice: Subject to any disclaimer, the term of this patent is extended or adjusted under 35 U.S.C. 154(b) by 0 days.

(21) Appl. No.: 12/071,580

(22) Filed: Feb. 22, 2008

(65) Prior Publication Data

US 2009/0216478 A1    Aug. 27, 2009

(51) Int. Cl.
G06F 19/00    (2006.01)

(52) U.S. Cl. ..................................... 702/104

(58) Field of Classification Search .................. 702/50, 702/104, 189; 356/56, 317
See application file for complete search history.

(56) References Cited

U.S. PATENT DOCUMENTS

| | | | |
|---|---|---|---|
| 6,897,954 B2 | 5/2005 | Bishop et al. | |
| 6,954,722 B2 | 10/2005 | Parks et al. | |
| 2006/0259253 A1 * | 11/2006 | Ellison et al. | 702/50 |

OTHER PUBLICATIONS

Howard M. Shapiro, "Practical Flow Cytometry" 3rd Edition, 1995, pp. vii-xxii, 17-19, 163-166 and 214-215, (Wiley-Liss, NY).
Mario Roederer, "Spectral Compensation for Flow Cytometry: Visualization Artifacts, Limitations, and Caveats", Cytometry, 2001, 45: 194-205.
C. Bruce Bagwell, et al., "Fluorescence Spectral Overlap Compensation for any Numbers of Flow Cytometry Parameters", Annals New York Academy of Sciences, 1993, 677: 167-184.
Mario Roederer, "Compensation is not Dependent on Signal Intensity or on Number of Parameters", Cytometry (Communications in Clinical Cytometry), 2001, 46:357, Wiley-Liss.

* cited by examiner

*Primary Examiner*—Bryan Bui
(74) *Attorney, Agent, or Firm*—Sterne, Kessler, Goldstein & Fox, PLLC.

(57) ABSTRACT

In an embodiment, a computer-implemented method is provided for processing digital data from a particle analyzer. The method includes receiving digital particle data, transforming the received data to correct for noise, applying linear compensation for dye spectral overlap, and re-establishing the original dimensions of the data. Processed particle data may be used for display, analysis or storage. In another embodiment, a system comprises at least one particle analyzer coupled to a particle data corrector. The particle data corrector includes a transformer, a compensator, and a converter.

14 Claims, 5 Drawing Sheets

Single-color run using Logicle (left) and using present invention (right).

Figure 3b

Single-color five-level run with linear compensation (left) and with present invention (right)

Figure 3c

Two-color run with linear compensation (left) and with present invention (right)

METHOD AND SYSTEM FOR PARTICLE DATA PROCESSING

BACKGROUND

The present invention relates generally to the field of particle analyzers, and more specifically to reducing noise in data collected from multi-parameter particle analyzers.

Particle analyzers enable analysis of properties of particles, for example, individual cells, by subjecting them to an excitation light and measuring the resulting scattered and/or emitted light as detected by one or more light detectors. Different types of particle analyzers, such as flow cytometers and scanning cytometers, are described in the art. In a flow cytometer, for example, the excitation light beams may be stationary, while analyte cells in a liquid flow through a point at which the light beams converge. A scanning cytometer scans a fixed cell population, for example, on a microscope slide, with one or more excitation light beams. Flow cytometers can also be equipped with sorting devices that have the added advantage of being able to separate individual cells in a sample for further culture or analysis.

Prior to being exposed to an excitation light, particles may be labeled (also referred to as marked) with spectrally distinct fluorescent dyes or fluorescent dyes conjugated to molecule-specific ligands. In a sample, each particle may bind with one or more fluorescent dyes and/or dye conjugates. For example, a single cell may bind with one or more fluorescent dyes conjugated to antigen-specific antibodies depending on the characteristics of the proteins that are elements of that cell. When an excitation light is focused on a cell in a flow cytometer, the cell may scatter and/or emit light in several directions. The pattern of the scattered and/or emitted light allows one type of cell to be distinguished from another. The resulting fluorescence pattern is generally indicative of defined characteristics of the particles under analysis. Samples of particles are generally labeled with multiple dyes or dye conjugates in order to identify a range of properties of the constituent particles. The measure of fluorescence of a particle that is not stained with any fluorescent dye, is known as the auto-fluorescence of that particle. However, while auto-fluorescence may enable the study of some properties of particles, by itself it is generally of limited use due to multiple factors including a fluorescence-level that is too low and the limited types of elements in a cell that may contribute to auto-fluorescence.

A particle analyzer may include multiple light detectors, and dyes are selected so that the peak fluorescence range of each dye is detected by a separate light detector. Due to the very low intensity of the kind of light emitted by small particles, these instruments are generally equipped with very sensitive detectors called photomultiplier tubes (PMTs) that can detect individual photons. The resulting fluorescence measurement is based on the number of the photons detected by each light detector.

The spectral range of each light detector in a particle analyzer is referred to as a "bin". The clarity of the detected fluorescence data, as measured by light detectors, is dependent on each bin substantially containing only the measurements for the dye having a peak fluorescence within that bin. When a particle labeled with more than one dye is subjected to an excitation light, the light emitted by each dye may spread over a wide spectral range centered at or near the peak fluorescence maximum. The range over which the resulting fluorescence spreads may exceed the spectral range of the corresponding bin, and may also be detected in adjacent bins. This effect is referred to variously as "spillover," "fluorescence spectral overlap," or "dye spectral overlap". The fraction of the signal that crosses over to another bin is known as the "spillover coefficient".

As the number of dyes are increased and/or the fluorescence range of each dye is increased, the spectral overlap among the bins increase. The resulting data may have bins for which substantial spillover occurs. Substantial amounts of spillover may limit the usefulness of the data for particle analysis.

Methods are known in the art for utilizing multicolor particle analyzer data despite the spillover issues. The methods are based primarily on compensating for the spillover effect in the data to alleviate issues of overlapping data measurements in different detectors. Although in some situations compensation may be performed manually using analogical electronic circuitry, current compensation systems for higher number of colors and detectors may require software implemented compensation methods to be practical. Compensating for a spillover effect may involve subtracting some numerical quantity from each detector other than the primary detector for that color. For example, if a particle with a primary detector p1 has a spillover coefficient of 0.3 with respect to a second detector p2, then 30% of p1 must be subtracted from p2. This kind of linear compensation for spillover effect, in a multicolor particle analyzer, may involve solving complex sets of linear equations. A number of linear compensation methods are discussed in Bagwell, C. B., and Adams, E. G., "Fluorescence Spectral Overlap Compensation for any Number of Flow Cytometer Parameters," Ann N.Y. Acad Sci. 677:167-84 (1993), and in Shapiro, H. M., "Practical Flow Cytometry," $3^{rd}$ edition, pp. 17-19, 163-166, 214-215 (Wiley-Liss, Inc., 1995).

Current linear approaches to digital compensation significantly improves the quality of the data analysis and often produces the desired two-dimensional orthogonal plot distribution that facilitates the identification of positive and negative particle populations. These known methods, prior to the invention, however, have limitations. Built into them, is an assumption that the spillover effects are linear, and therefore can be compensated for by such linear mathematical methods. Frequently when bright signals are detected using fluorescent dyes with relatively large spillover coefficients, a substantial amount of noise with non-linear characteristics remains after the compensation process.

Due to the large dynamic range of the measured fluorescence signal intensities, often in the range of four log decades or 10,000:1, linear display of a large amount of data would be of little clarity, particularly in the presence of spillover. In general, an exponential curve in the linear domain, appears as a linear curve in the logarithmic domain. The logarithmic scale is therefore able to display a large dynamic range such as 10,000:1 and is used very frequently to display and analyze particle data. However, particle analysis data containing noise that makes it deviate from linear behavior, once subjected to compensation, may contain a number of negative data points. Mathematically such negative data points are undefined on a logarithmic scale and are often lost or just shown as a collection of points on a display axis, limiting the usefulness of those data points to the analysis. On the other hand, abnormal data spreading due to non linear noise can produce visualization artifacts that produce false results at the moment to evaluate particle characteristics. More details on these issues can be found in Roederer, M., "Spectral Compensation for Flow Cytometry: Visualization Artifacts, Limitations, and Caveats," Cytometry 45:194-205 (2001).

Known methods for utilizing particle data containing spillover issues as the previously discussed include a number of display oriented methods. For example, scaling systems, such as the biexponential model (Logicle) display described in U.S. Pat. No. 6,954,722, rely upon display techniques to present a useful display of the data addressing some issues of the pure logarithmic scale display discussed above. The biexponential model applies a linear scaling for lower intensity data points and a logarithmic scaling for higher intensity data points that alleviates the problem of inability to show negative data points in a pure logarithmic scaled display. However, the methods described in the art, while helping to clarify the raw data received from a particle analyzer, do not yield sufficiently low-noise-data for analysis. They do not address the root causes of the non linear data spreading and so can not solve the issue of establishing consistent positive/negative boundaries and determining accurate fluorescence values to prevent false positives.

A primary cause of the remaining non-linear noise is photon counting statistics error, also known as photon count statistic noise or shot noise. Photon counting statistics error refers to the error inherent in counting of photons captured by light detectors. See Roederer, supra, for additional information. Applying linear compensation by subtracting a percentage of the measured signal value at the primary detector from the measured value at a non-primary detector based on observed intensities, may result in reducing the measured value at the non-primary detector well beyond the linear spillover component. This aberration of the data caused by the remaining non-linear noise is particularly evident when the data is displayed in a logarithmic scale. Such overcompensation is likely because the subtracted value may have included a factor for the non-linear photon counting statistics error in addition to the linear spillover compensation factor. That remaining noise further complicates data analysis, and leads to identification of false positive populations. What is needed therefore, is a method and system, to substantially remove remaining noise components of particle data, particularly non-linear photon counting statistics error.

SUMMARY

The present invention relates to particle analysis and data processing. In one embodiment, a computer-implemented method for processing digital data from a particle analyzer is provided. Raw particle data is first transformed to have reduced noise, then compensated for dye spectral overlap, and thereafter converted to re-establish dimensions corresponding to the raw data. The converted particle data may be then output for display or storage.

Another embodiment is a system for displaying and analyzing particle data. The system includes at least one particle analyzer; a particle data corrector that includes a transformer, compensator and a converter; and a display.

Yet another embodiment is computer program product for causing a computer to process raw particle data. The computer program product includes program code that enables the computer to transform raw particle data to have reduced noise, program code that enables the computer to compensate for dye spectral overlap, and program code that enables the computer to generate particle data having dimensions of the raw particle data.

Further features and advantages of the present invention, as well as the structure and operation of various embodiments thereof, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

FIG. 3 shows side by side comparisons of logarithmic scaled displays of particle data obtained using an embodiment of the present invention and other methods.

The features and advantages of the present invention will become more apparent from the detailed description set forth below when taken in conjunction with the drawings. In the drawings, like reference numbers generally indicate identical, functionally similar, and/or structurally similar elements. Generally, the drawing in which an element first appears is indicated by the leftmost digit(s) in the corresponding reference number.

DETAILED DESCRIPTION

The present invention relates to particle analysis data processing. While the present invention is described herein with reference to illustrative embodiments for particular applications, it should be understood that the invention is not limited thereto. Those skilled in the art with access to the teachings herein will recognize additional modifications, applications, and embodiments within the scope thereof and additional fields in which the invention would be of significant utility.

Figure 1:
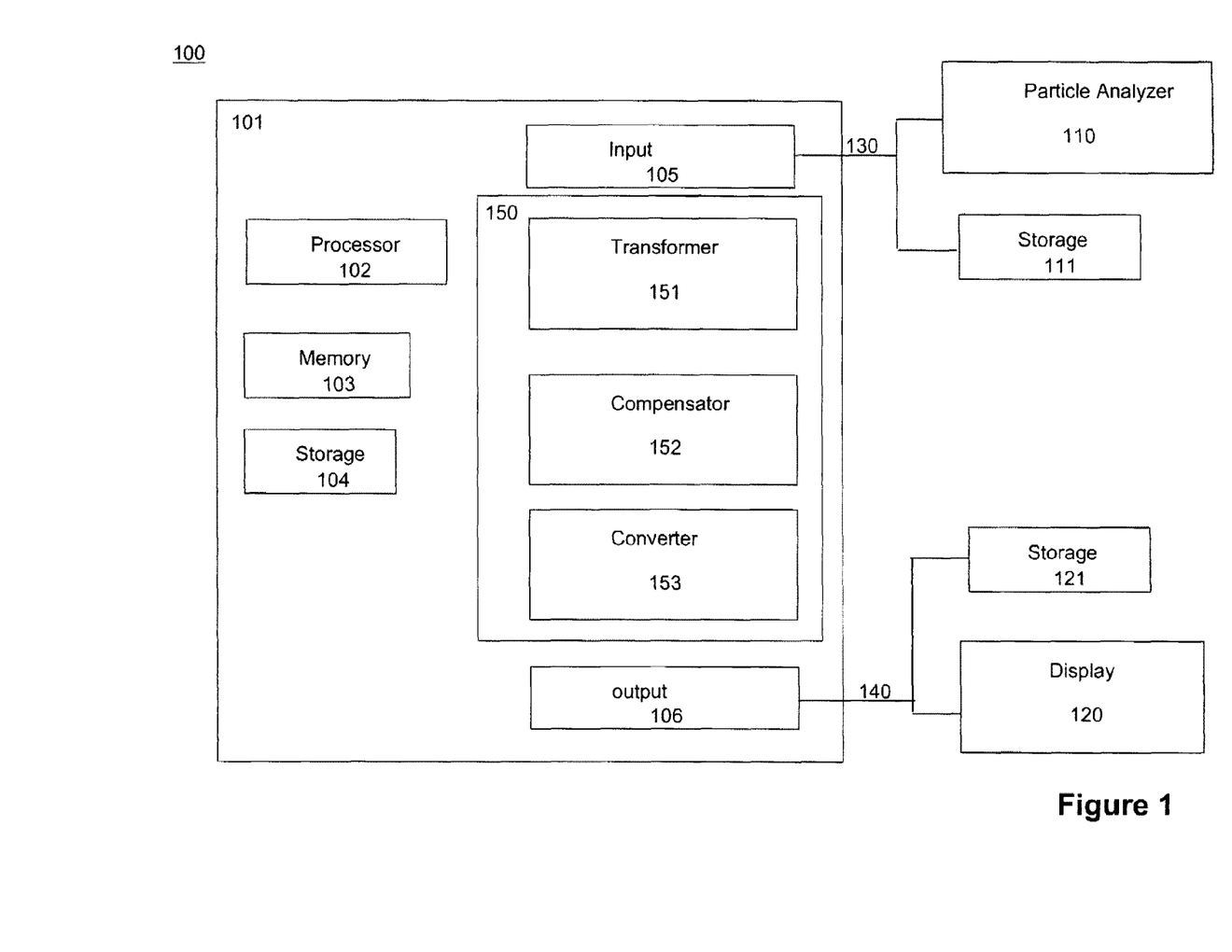
FIG. 1 illustrates a system for processing particle analyzer data according to an embodiment of the present invention.

FIG. 1 illustrates a system 100 for processing and analyzing particle data according to an embodiment of the present invention. A computer 101 is coupled through link 130 to a particle analyzer 110 and a storage device 111. Computer 101 is also coupled, through link 140, to display device 120 and storage device 121. One skilled in the art will understand that the links 130 and 140 may represent communication paths internal to a single computer, or connectivity provided by one or more networks such as a local area network or wide area network.

Computer 101 may be any type of computing or data processing device. In one example computer 101 includes a processor 102, a memory 103, a storage device 104, an input module 105, an output module 106, and a particle data corrector module 150. Particle data corrector module 150 may further include a transformer module 151, a compensator module 152, and a converter module 153. The functionality of modules 151-153 is further described below. One skilled in the art will recognize that modules 151-153 may be implemented entirely in software, hardware or using combinations of software and hardware. For example, some of the functionality herein may be implemented with the assistance of a specialized field programmable gate array (FPGA) or digital signal processor (DSP). Logic instructions, including software computer programs implementing some or all of the functionality of modules 105, 106, 151-153 may be encoded in a computer usable medium including but not limited to a DVD, a CD-ROM, a floppy disk, a tape, a flash memory device or component, a system memory device or component, or hard drive. A person skilled in the art will understand that computer 101 may include multiple computing or data processing devices that are located on the same or different platforms at the same or different locations.

Processor 102 may execute all software processing in computer 101, and may also be responsible for the coordination of any hardware components. In another embodiment, computer 101 may include multiple processors for executing software. Memory module 102 may be implemented as random access memory (RAM) and may store execution instructions, and data being processed. For example, memory module 102 may hold particle data input to computer 101 during the processing of that data in particle data corrector module 150. Internal storage device 104 may store converted particle data output by particle data corrector module 150. In other embodiments, storage device 104 may serve to temporarily store data being processed by particle data corrector module 150.

Input module 105 and output module 106 may include a combination of hardware and software components enabling computer 101 to receive raw particle data and to output processed particle data respectively. For example, input module 105 may include a network interface device and the associated software to receive incoming data and make that data available to particle data corrector module 150. Likewise, for example, output module 106 may include an output network interface device as well as software for sending the converted particle data output by particle data corrector module 150 on link 140 to display device 120 or storage device 121.

Particle analyzer 110 may be any device, including a flow cytometer, that measures a signal based on a count of either photons or electrons, for example photons scattered by an excitation light projected on one or more particles under analysis detected by a PMT. Particle analyzer 110 may also be a scanning cytometer or other particle analyzer, for example and without limitation, that make measurements based on the count of fluorescence photons emitted under excitation by light beams. Storage device 111 may, in some embodiments, store the raw digital data (raw particle data) output from particle analyzer 110. Raw particle data is input to particle data corrector module 150 through input module 105. In one embodiment, the raw particle data may be received at input module 105 directly from particle analyzer 110. In another embodiment, data generated by particle analyzer 110 may be stored in storage device 111 before being received at input module 105.

The processed particle data output from computer 101 through output interface 106, in one embodiment, may be received by display device 120. Display device 120 may be a graphical user interface capable of displaying particle analyzer data according to one or more display techniques, including a logarithmic scale, a linear scale, or biexponential display as in Logicle. One skilled in the art will understand that display device 120 may include other modules necessary to receive and display and/or analyze the data output from output module 106. In another embodiment, the data output from computer 101, may be directed to a storage device 121. The converted particle analyzer data thus stored in device 121 may later be used for further analysis or display. Storage device 121 can be coupled to computer 101 over any type of communications link. Accordingly, device 121 can be located at the same local site as computer 101 or at a different remote site. Similarly, display and analysis device 120 can be located at the same local site as computer 101 or at a different remote site.

Particle data corrector 150 includes, a transformer module 151, a compensator module 152, and a converter module 153. Transformer module 151 transforms the raw particle data to generate transformed particle data having reduced noise. Compensator module 152 compensates the transformed particle data to generate compensated particle data having reduced dye spectral overlap. Converter module 153 converts the compensated particle data to generate converted particle data having dimensions conforming to the original dimensions of the raw particle data, where original dimensions include the range of values represented in the raw particle data.

Figure 2:
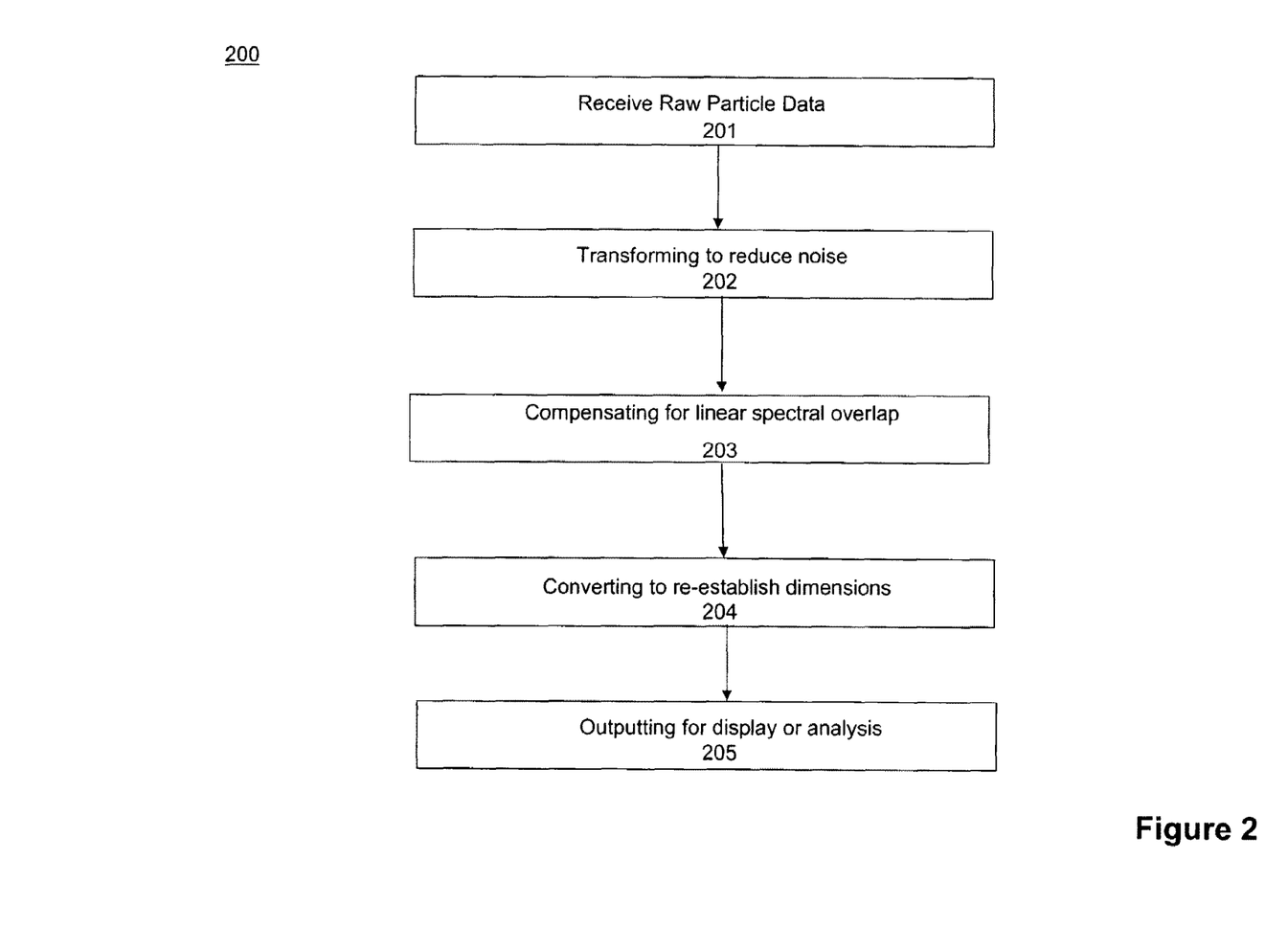
FIG. 2 is a flowchart of a method of processing particle analyzer data according to an embodiment of the present invention.

FIG. 2 illustrates a method 200 for processing digital data from a particle analyzer according to an embodiment of the present invention (steps 201-205). For brevity, method 200 will be described with reference to system 100 and its components; however method 200 is not necessarily intended to be limited to system 100. Steps 202, 203, and 204 may correspond to processing in the particle data corrector 150, specifically in modules 151, 152, and 153. In step 201, raw particle data is received, in one example, from input module 105. The raw particle data includes, for example, high resolution data from a particle analyzer. The raw particle data may include noise and dye spectral overlap. In step 202, the raw particle data is transformed to reduce noise, for example in module 151, generating transformed particle data. In step 203, the transformed particle data is compensated to eliminate or significantly reduce the effect of the spectral overlap, for example in module 152, generating compensated particle data, and in step 204 the compensated particle data is converted, for example in module 153, to re-establish the original dimensions of the raw particle data, generating converted particle data. Steps 201-204 are described below in greater detail with reference to modules 151-153. The converted particle data is output in step 205, for example by the output module 106 over the link 140 for storage in storage device 121 or display in display device 120. The data output in step 205 may be substantially free of noise and dye spectral overlap.

The raw particle data may have undesirable noise and dye spectral overlap inherent in the data. The spectral overlap for each dye, as is known in the art, linearly increases with the signal intensity. Due to this linear relationship, the spreading caused by dye spectral overlap is reducible using one of several known methods including linear compensation. The noise component in the raw digital particle data may also include photon counting statistics error, measurement or binning error and other electronic and optical noise. In most modern particle analyzers, the noise due to binning, electronics and optics is relatively small. In general, the most significant component of the noise, for example, in flow cytometry particle data, is the photon counting statistics error. In contrast to dye spectral overlap, it is known that the photon counting statistic error is non-linear with respect to signal intensity. The increase in the photon counting statistic error follows Poisson's distribution, and the standard deviation of Poisson's distribution increases with the square root of the measured variable. Therefore, the increase in photon counting statistics error may be characterized by the square root of the signal intensity or photon count. Because the noise due to photon count statistic error is mathematically definable, an appropriate adjustment may be made to the corresponding photon count so as to correct for the noise.

In an embodiment, transformer module 151, comprises logic instructions implementing a first mathematical model to transform the raw particle data (step 202), to obtain transformed particle data having reduced noise. For example, the first mathematical model may include one or more functions to correct for photon counting statistics error that is a major component of noise. Towards that end, the first mathematical model may include a mathematical function such as a power function of the form $y=a_1x^n+a_0$, or any other function that has mathematical behavior similar to a power function, for example, a root function of the form $y=a_1x^{1/n}+a_0$, or a polynomial function of the form $y=a_nx^n+a_{n-1}x^{n-1}+ \ldots +a_1x+a_0$, where $a_0 \ldots a_n$ and n are real numbers. For example, equation (1) may be used as the mathematical model for transforming raw particle data to reduce noise, particularly to reduce photon counting statistic error:

$$y=SQRT(x)-C \qquad (1)$$

where SQRT(x) is the square root of the signal of each parameter or fluorescence intensity of dye x for a given particle, and C is a constant characteristic of the particle analyzer. The value of C may be predetermined for a given particle analyzer. For example, in a flow cytometer C is equal to the square root of the average of the signal intensity of a population of non stained cells. A person skilled in the art given this description will understand that additional mathematical functions may be implemented in transformer module 151 to correct for noise components other than photon counting statistics error.

Compensator module 152, comprises logic instructions implementing a linear compensation method to compensate the transformed particle data for dye spectral spillover in step 203, to obtain compensated particle data. As discussed above, dye spectral spillover is generally a major cause of spreading in the raw particle data. A number of methods, including linear mathematical functions, are described in the art for reducing dye spectral spillover, for example, See Shapiro, supra, and Bagwell, supra. For example, in particle data with two color parameters, the linear relationship of the dye spectral overlap of each dye to the corresponding signal intensity allows the creation of a two-by-two cross-over matrix where the elements of each row comprises the signal measured at the corresponding primary detector and the spillover of that signal in the corresponding non-primary detector. Thereafter, the cross-over matrix may be inverted to create a compensation matrix, that is in turn multiplied with a matrix defining particle data input to the compensator module 152.

The operations of transformer module 151 affects original dimensions of the raw particle data. For example, a dynamic range in the raw data of 10,000:1 prior to the operation of module 151, may be reduced to 100:1 subsequent to the operation of module 151. Converter module 153 comprises logic instructions that implement a second mathematical model that may be the inverse of the first mathematical model implemented in transformer module 151. The operation of converter module 153, in step 204, is intended to re-establish the original dimensions of the particle data, as they were prior to being transformed by transformer module 151. The second mathematical model may include a mathematical function chosen so as to be the inverse of the first mathematical model, implemented in the same embodiment, in transformer module 151. Power functions, such as square functions or polynomial functions, may be included in the second mathematical model. For example, corresponding to the choice of equation (1) above, one may implement the inverse of equation (1) shown in equation (2) below:

$$x = \frac{|y+C|}{y+C}(y+C)^2 \qquad (2)$$

where x, y, and C is defined as in equation (1) above.

The second mathematical model implemented in converter module 153 may, in some embodiments, include other mathematical functions designed to re-establish the dimensions of the particle data. The output of converter module 153 is converted particle data, that may be either displayed using general means of display for particle data stored in memory or sent to another location. The converted data as output by output module 106, is already compensated for dye spectral overlap and is also corrected by removing noise, for example, particularly photon counting statistics error. The particle data itself has been corrected, compensated, and then the original dimensions re-established, so that the output of output module 106 may be displayed or analyzed using displays and/or analysis tools that are commonly used in the field of particle analysis, for example, logarithmic scales. Although the output of output module 153 may be displayed using a biexponential display, it may be superfluous because the spreading effect has already been reduced in the particle data itself.

A device implementing an embodiment of the present invention may include a disconnection feature that gives a user the ability to elect to exclude or disconnect transformer module 151 and converter module 153 from the processing path. In the event that the user excludes modules 151 and 153 from the processing path, the resulting data output from particle data corrector module 150 would only have been subjected to linear compensation in compensator module 152. A disconnection feature as described is useful in situations where the analysis may not be benefited by modules 151 and 153, for example, as when very high signal intensities beyond a predetermined threshold are observed, and the photon counting statistics error is no longer guaranteed to mathematically correspond to Poisson's distribution. Alternatively, modules 151 and 153 can be omitted.

Figure 3A:
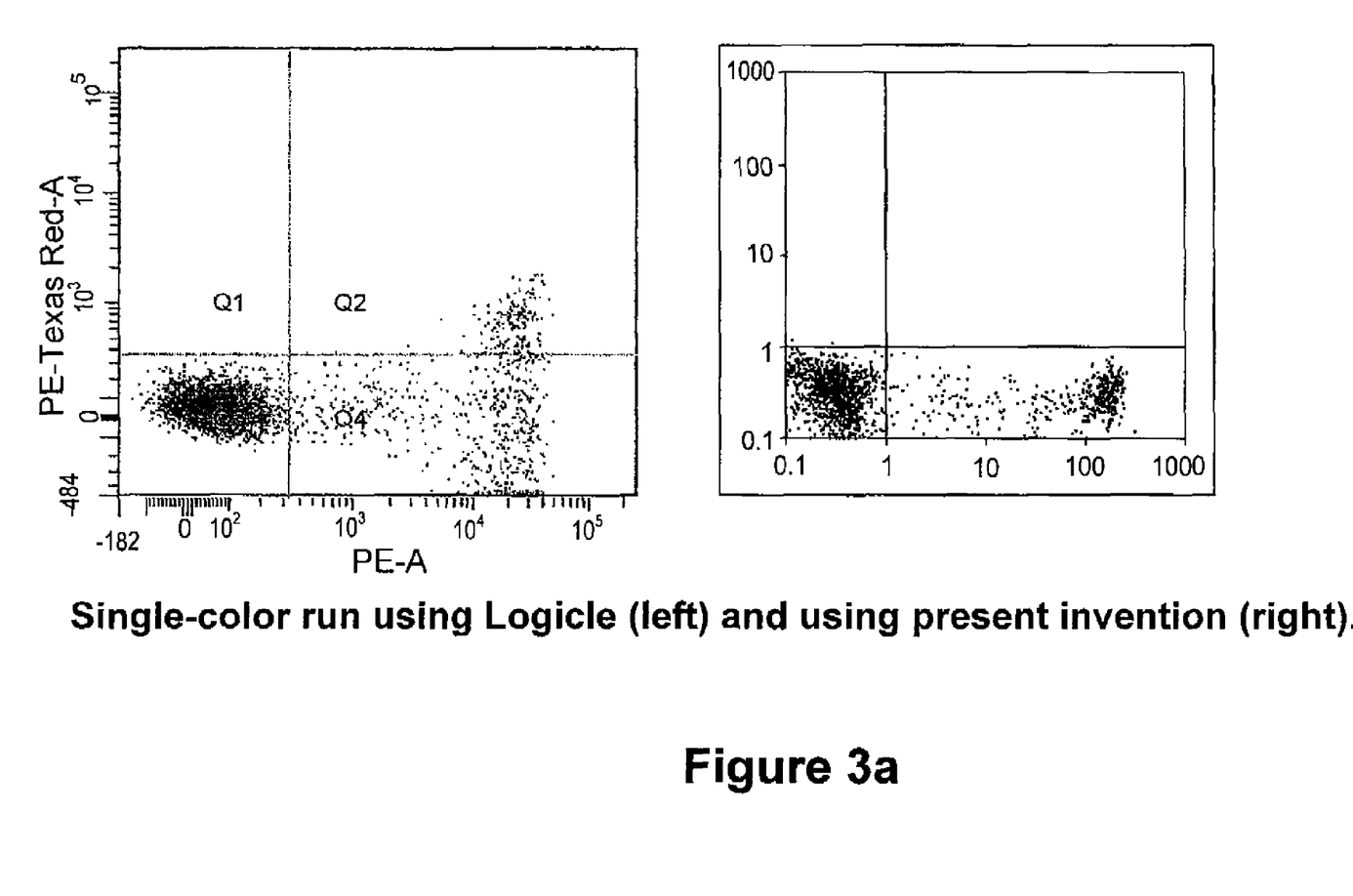
FIG. 3a shows a comparison between an embodiment of the present invention, and a biexponential display visualization of a single color run.
Figure 3B:
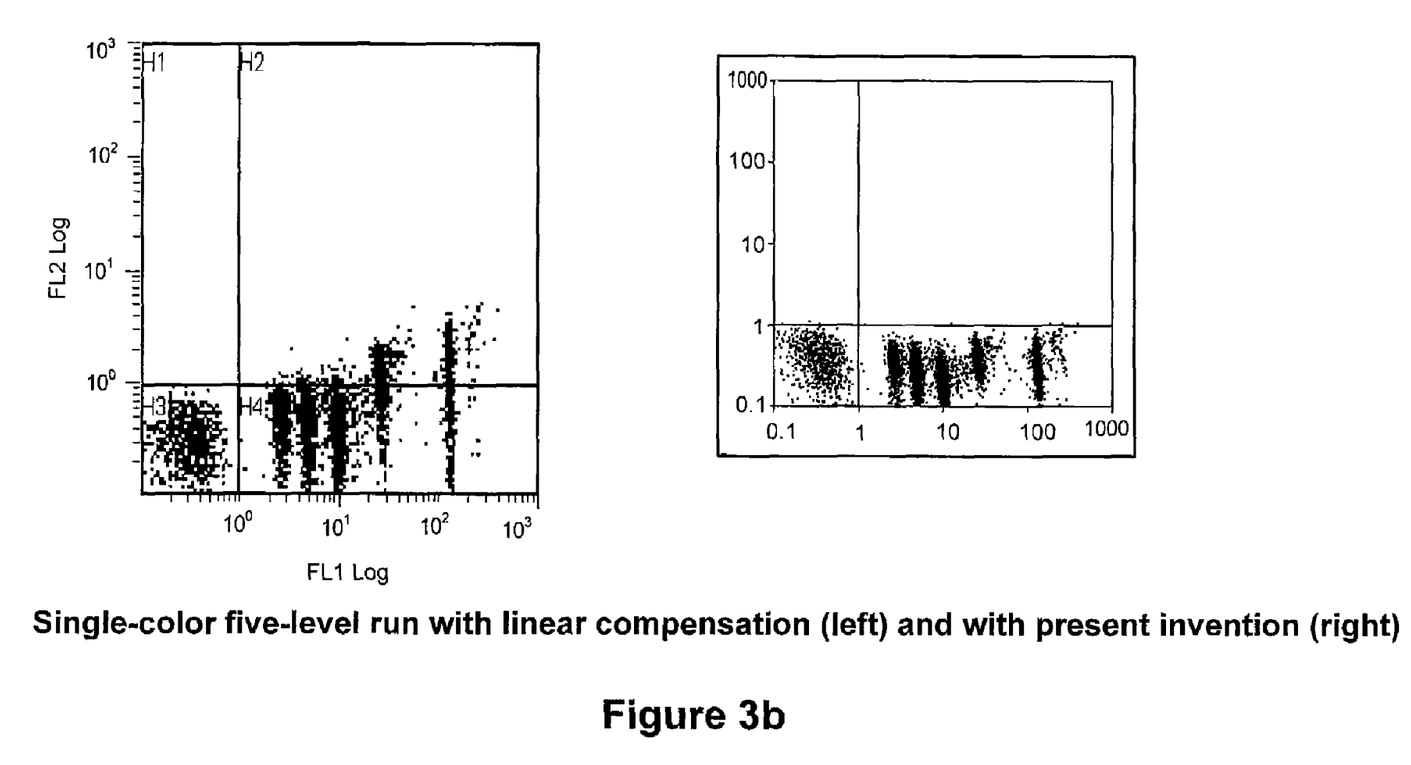
FIGS. 3b and 3c compares an embodiment of the present invention and linear compensation only approach in a single color five-fluorescence-intensity-levels bead run, and a 2 color run respectively.
Figure 3C:
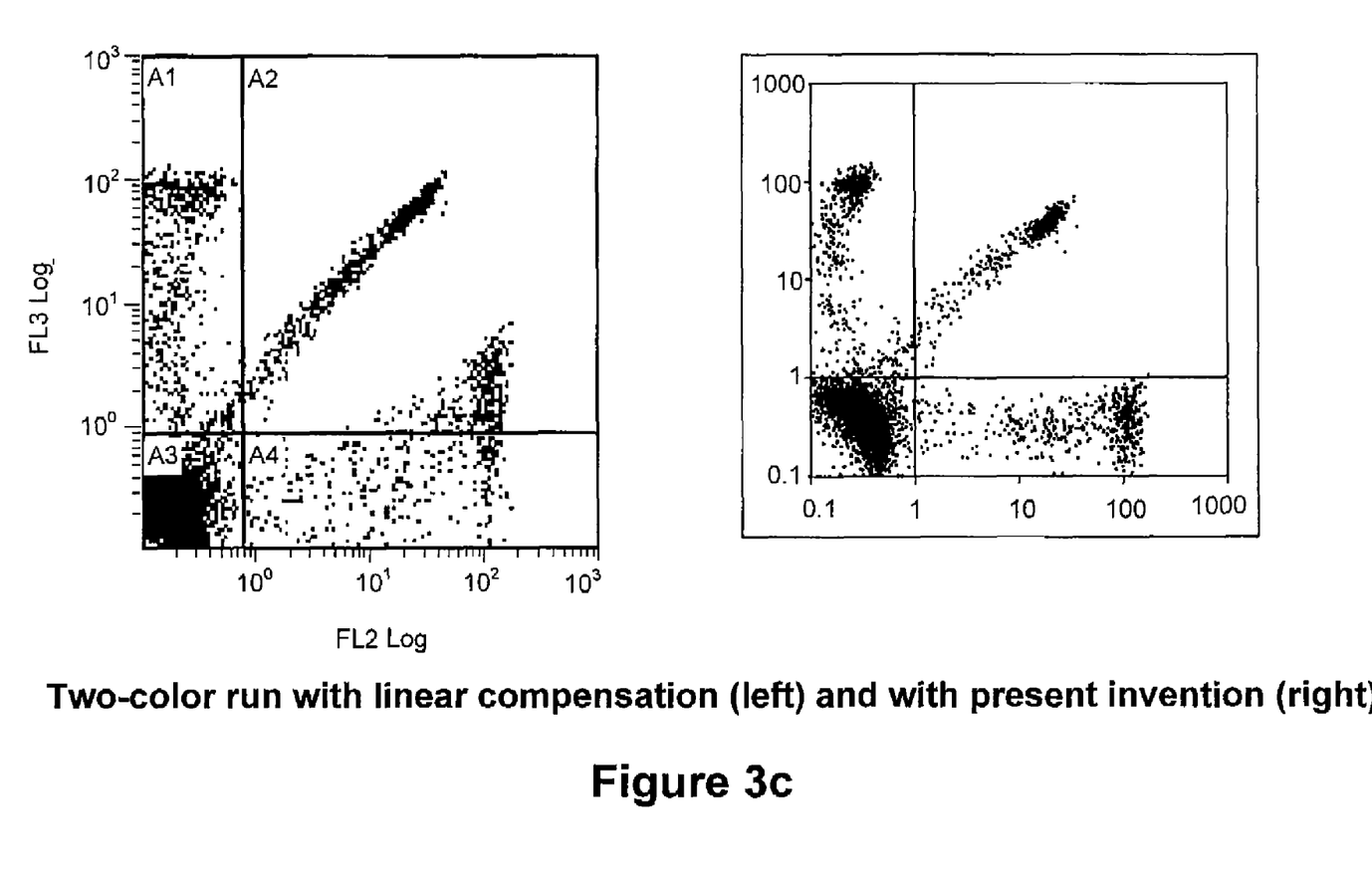

In FIG. 3 side-by-side comparisons of results obtained using an embodiment of the present invention and selected currently available art is shown. FIG. 3a shows the results of corresponding single color flow cytometry runs, using the biexponential mode display of Logicle (left) and an embodiment of the present invention (right). The graph illustrating the embodiment of the present invention displays a clear level of population concentration, where both identifiable populations are identifiable with respect to the color being measured. The population in the lower left quadrant represents the negative population that has very little fluorescence in the color being measured. The Logicle graph on the other hand, shows the spreading that occurs particularly relative to the positive population concentration. The vertical spreading of the positive population in the graph on the left may be attributable primarily to photon count statistics error. In FIG. 3b, the results of a single color five bead run is shown where only linear compensation is applied (left) and where data is processed to reduce non-linear noise effects in accordance with an embodiment of the present invention (right). Again, significant spreading is shown in the positive populations, when only linear compensation is applied. The display according to the embodiment of the present invention eliminated the spreading almost entirely. In FIG. 3c, results are shown for a two-color flow cytometry run applying only linear compensation (left) and in addition, reducing the non-linear noise components using and embodiment of the present invention (right). In the display applying only linear compensation, the spreading of the population towards the lower right is clear. The present invention, in an embodiment, has successfully eliminated the spreading indicated in the graph on the left. It should be noted that the spreading within, for example, the lower right quadrant of the graph on right, is valid data and is due to normal particle variation. Given this description, one skilled in the art will understand that, as illustrated in FIG. 3, embodiments of the present invention may substantially reduce compensation artifacts in digital particle data.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A computer-implemented method for processing digital data from a particle analyzer, comprising:
   receiving raw particle data from the particle analyzer at a computer, wherein the raw particle data has noise including photon counting statistics error;
   transforming the raw particle data to obtain transformed particle data having reduced photon counting statistics error;
   compensating the transformed particle data for dye spectral overlap, to obtain compensated particle data;
   converting the compensated particle data to obtain converted particle data, having dimensions conforming to the raw particle data; and
   outputting the converted particle data.

2. The method of claim 1, further comprising displaying the converted particle data.

3. The method of claim 1, further comprising storing the converted particle data.

4. The method of claim 1, wherein the transforming comprises using at least one mathematical function to obtain the transformed particle data.

5. The method of claim 4, wherein the converting comprises using at least one function that is the inverse of said mathematical function.

6. The method of claim 1, wherein compensating the transformed particle data for dye spectral overlap comprises using at least one linear mathematical function.

7. The method of claim 2, wherein the displaying includes displaying the converted data using a logarithmic scale or biexponential scale.

8. A system for processing particle data from at least one light detector, comprising:
   at least one particle analyzer;
   a particle data corrector that receives from the at least one particle analyzer raw particle data having noise including photon counting statistics error;
   a display device, wherein the display device is coupled with the particle data corrector; and
   wherein the particle data corrector includes:
   a transformer that transforms the raw particle data to generate transformed particle data having reduced photon counting statistics error;
   a compensator that compensates the transformed particle data to generate compensated particle data having reduced dye spectral overlap; and
   a converter that converts the compensated particle data to generate converted particle data having dimensions conforming to said raw particle data.

9. The system of claim 8, wherein the particle analyzer comprises a flow cytometer.

10. The system of claim 8, wherein the transformer applies at least one mathematical function to obtain the transformed particle data.

11. The system of claim 10, wherein the converter applies at least one function that is the inverse of the said mathematical function.

12. The system of claim 8, wherein the compensator applies at least one linear mathematical function.

13. A system for reducing noise in raw particle data generated from at least one light detector, the noise including photon counting statistics error, said system comprising:
   a transformer that transforms the raw particle data to generate transformed particle data having reduced photon counting statistics error;
   a compensator that compensates the transformed particle data to generate compensated particle data having reduced dye spectral spillover effects;
   a converter that processes the compensated particle data to generate converted particle data having dimensions conforming to said raw particle data; and
   an output interface that outputs the converted particle data.

14. A computer program product comprising a computer usable medium having control logic stored therein for causing a computer to process raw particle data from at least one light detector, the raw particle data having noise including photon counting statistics error, said control logic comprising:
   first computer readable program code that enables the computer to transform the raw particle data to generate transformed particle data having reduced photon counting statistics error;
   second computer readable program code that enables the computer to compensate the dye spectral overlap of the corrected particle data to generate compensated particle data;

third computer readable program code that enables the computer to convert the compensated particle data to generate converted particle data having dimensions of the raw particle data; and fourth computer readable program code to enable the computer to output the converted particle data.

* * * * *